(12) United States Patent
Wood et al.

(10) Patent No.: US 6,414,311 B1
(45) Date of Patent: Jul. 2, 2002

(54) SPECTROMETER ACCESSORY FOR CARRYING OUT ATTENUATED TOTAL REFLECTANCE MEASUREMENTS

(75) Inventors: Christopher Wood, Tring; Ian Alcock, Hemel Hampstead, both of (GB)

(73) Assignee: Wellesley International C.V. (CH)

( * ) Notice: Subject to any disclaimer, the term of this patent is extended or adjusted under 35 U.S.C. 154(b) by 0 days.

(21) Appl. No.: 09/383,243

(22) Filed: Aug. 26, 1999

(30) Foreign Application Priority Data

Aug. 28, 1998 (GB) .......................................... 98306956

(51) Int. Cl.$^7$ ............................................... G01N 21/35
(52) U.S. Cl. .................................................. 250/339.08
(58) Field of Search .................................... 250/339.08

(56) References Cited

U.S. PATENT DOCUMENTS 5,015,092 A   5/1991  Sting .......................... 356/300
5,106,196 A * 4/1992  Brierley ...................... 356/445
5,210,418 A   5/1993  Harrick et al.
5,945,674 A * 8/1999  Dukor ..................... 250/339.11

FOREIGN PATENT DOCUMENTS

| EP | 0341927 | 11/1989 | .......... G01N/21/75 |
| WO | 8606834 | 11/1986 | .......... G01N/21/41 |
| WO | 9314391 | 7/1993  | .......... G01N/21/55 |

* cited by examiner

*Primary Examiner*—Constantine Hannaher
(74) *Attorney, Agent, or Firm*—St. Onge Steward Johnston & Reens LLC

(57) ABSTRACT

An accessory for carrying out ATR measurements in a spectrometer such as an FT-IR spectrometer. The accessory has input optical elements for directing a beam of infra-red radiation to an HATR crystal 75 and output optical elements for directing radiation leaving the crystal towards an IR detector. The optical elements include a pivotable element which is adjustable automatically to a position in which it causes the radiation to be incident on the crystal at an angle of incidence appropriate for that crystal.

5 Claims, 7 Drawing Sheets

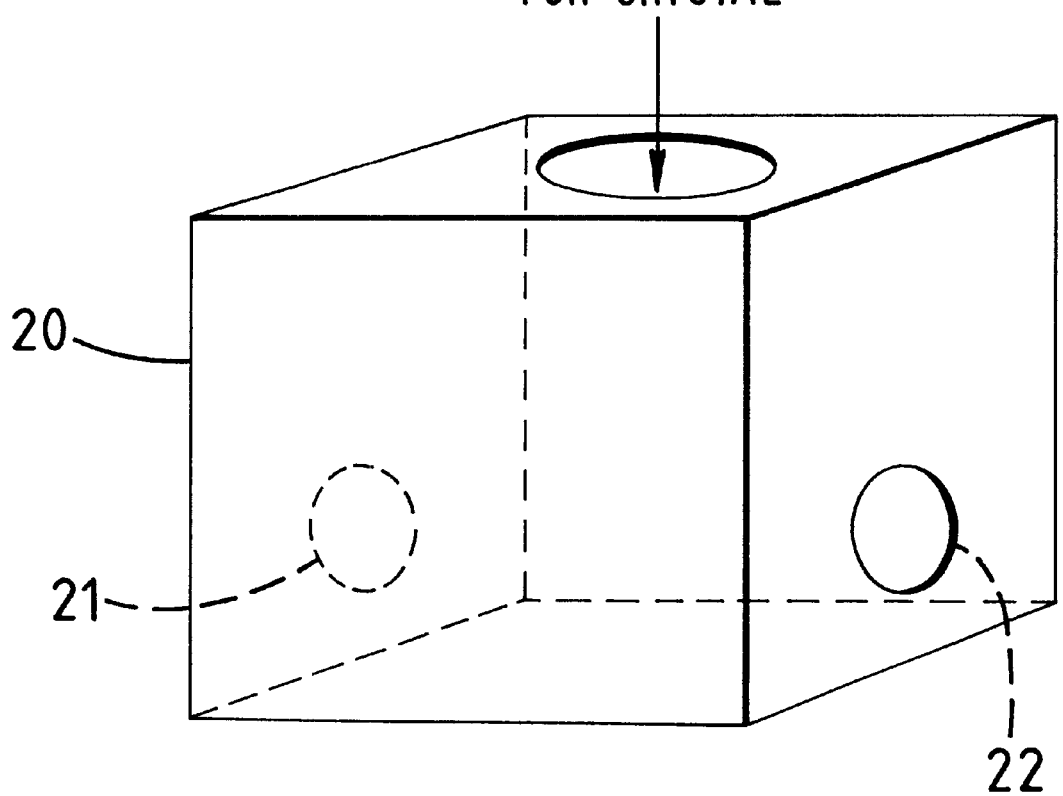

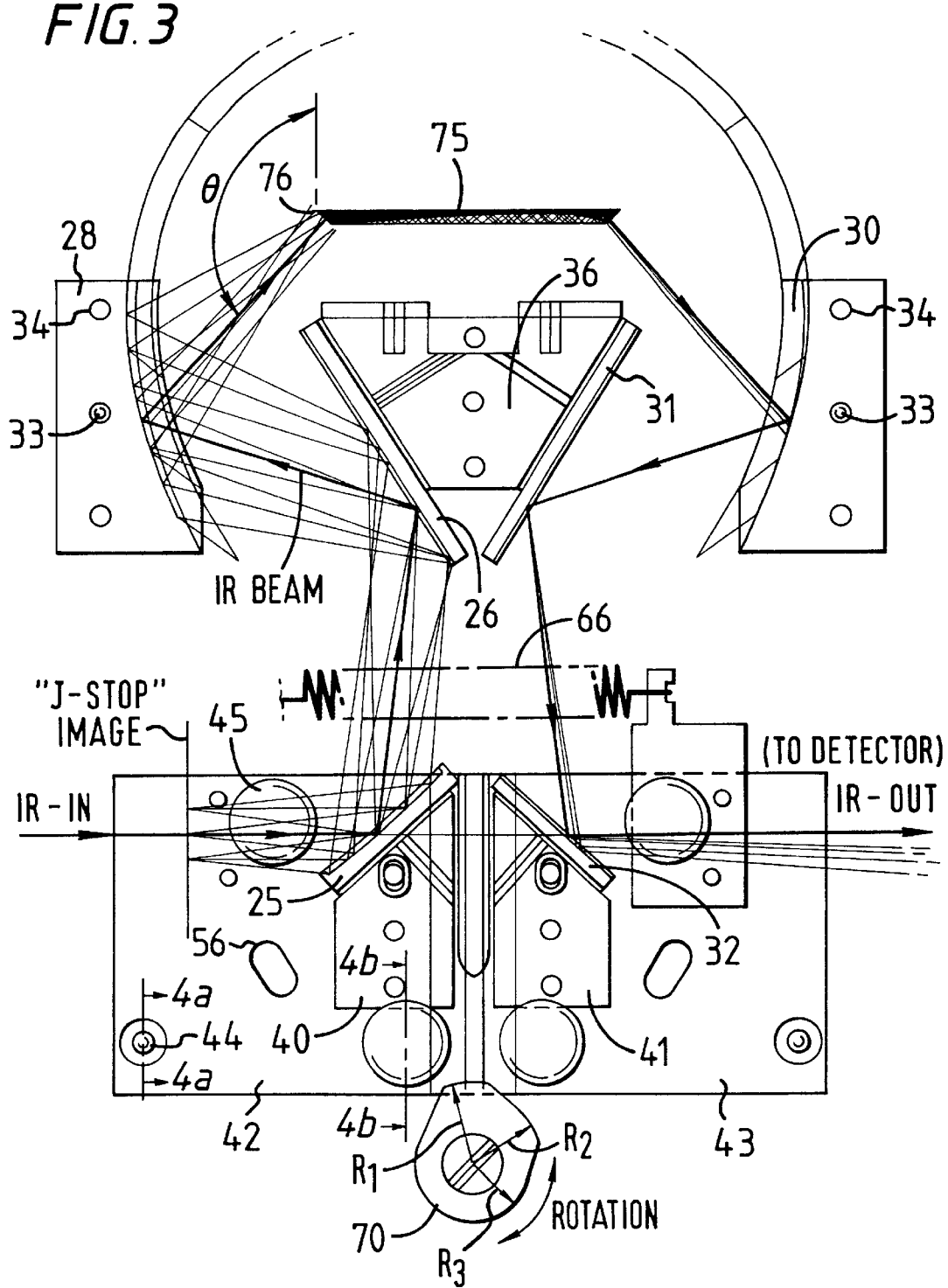

SPECTROMETER ACCESSORY FOR CARRYING OUT ATTENUATED TOTAL REFLECTANCE MEASUREMENTS

FIELD OF THE INVENTION

This invention relates to an accessory which can be used with a spectrometer in order to carry out attenuated total reflectance (ATR) measurements. In particular the invention relates to an accessory which can carry out horizontal attenuated total reflectance (HATR) measurements using a crystal in which multiple reflections of the analysing radiation occur.

BACKGROUND ART

In the field of spectroscopy such as FT-IR spectroscopy, it is known when poorly reflecting samples are being analysed to use what is called an attenuated total reflectance (ATR) technique. This usually involves mounting in the spectrometer an accessory which incorporates a crystal which utilises total internal reflectance or attenuated total internal reflectance. The sample is located in contact with a crystal which is to be analysed and contact between the sample and the crystal is usually maintained by the application of pressure to the crystal or the sample in the case of a solid sample.

One known type of crystal is an elongate crystal of generally trapezoidal shape which is used to carry out what is commonly known as horizontal attenuated total reflectance measurements. When using such a crystal analysing radiation enters the crystal through one of its inclined end faces and undergoes multiple internal reflections along the length of the crystal before exiting the crystal through its other inclined face. Such a crystal can be used to carry out an analysis of both solids and liquids. The sample under investigation is placed in close contact with one of the plane surfaces of the crystal and the analysing radiation slightly penetrates the sample at its point of contact with the crystal as the radiation undergoes multiple reflections along the length of the crystal. By analysing the radiation exiting from the crystal it is possible to produce a spectrum of the sample under investigation.

It is known to vary the angle of incidence of the radiation on the crystal end face in order to change the penetration depth of the analyzing radiation and it is known also to use crystals of different dimensions according to the particular analysis being carried out. When a change of crystal or a change of angle of incidence is required it is usually necessary to change the optics of the arrangement in order to ensure the analyzing radiation enters the crystal at the correct angle. Conventionally this has been carried out manually and is a somewhat tedious operation. Furthermore the adjustment are not accurately repeatable and this can affect the accuracy of measurements.

Additionally, it has been difficult to achieve a reliable and consistent way of applying force to the crystal or sample in order to ensure the appropriate contact between the crystal and the sample under investigation.

SUMMARY OF THE INVENTION

The present invention is concerned with an accessory for carrying out horizontal attenuated total reflection measurements in which optical elements can be adjusted automatically when a change of crystal is required.

Additionally, the invention provides an arrangement in which a reliably reproducible force can be applied to the crystal or sample to maintain contact between the crystal and the sample under investigation.

According to the present invention there is provided an accessory for use with a spectrometer which has a sample station in which the accessory can be located, said accessory comprising a mounting for receiving an ATR crystal, first optical elements for directing an incoming beam of analysing radiation to said crystal, second optical elements for directing a beam of radiation exiting the crystal to an outlet, at least one of the first optical elements and at least one of the second optical elements being pivotable, and means operable to cause equal and opposite pivoting movement of said pivotable elements so that the beam of analysing radiation is caused to be incident on said crystal at an angle appropriate for particular crystal employed or the measurement to be made.

The first optical elements may include a first mirror fixed to a first plate which is pivotally mounted on the housing of the accessory, the second optical element may include a second pivotable mirror mounted on a second plate which is pivotally mounted on the housing of the accessory. The pivoting means may comprise a rotatable cam member disposed at least partially between and in contact with said plates. The cam member may include a plurality of angularly spaced portions of different radii whereby rotation of the cam member causes said plates to assume an orientation which is different according to which portion of the cam member contacting said plates.

The cam member may be rotatable by a motor. The motor may be a stepper motor.

The first mirror may be a toroidal mirror and the second mirror may be a planar mirror.

The accessory may include electrical connectors which when the accessory is located in the sample station make contact with a connector on the spectrometer and the crystal it may have incorporated therein a data storage medium in which is stored data indicative of the crystal, the arrangement being such that when the accessory is located in the sample station the processor of the spectrometer can read said stored data and can transmit energising signals to said motor to cause the pivotable mirrors to be adjusted to a position appropriate to the crystal.

The first optical elements may also include a fixed plane mirror and a fixed toroid/ellipsoidal mirror, and the second optical elements may also include a fixed toroidal/ellipsoidal mirror and a fixed planar mirror.

The accessory may include an arm mounted on said housing, said arm including pressing means contactable with said crystal or a sample located adjacent said crystal in order to apply pressure to said crystal to maintain contact between the crystal and a sample under investigation. Pressure measuring means may be associated with said arm. The pressure measuring means may comprise a strain gauge. The strain gauge may be electrically connectable to said processor of said spectrometer in order to enable data relating to the applied pressure to be transmitted to said processor. A display means may be provided to display the sensed pressure thereby enabling an operator to accurately set the optical pressure.

BRIEF DESCRIPTION OF THE PREFERRED DRAWINGS

The invention will be described now by way of example with particular reference to the accompanying drawings. In the drawings:

FIG. 2 is a perspective view of an accessory.

FIG. 3 is a front elevational view showing the principal elements of the accessory.

DETAILED DESCRIPTION OF THE PREFERRED EMBODIMENT

Figure 1:
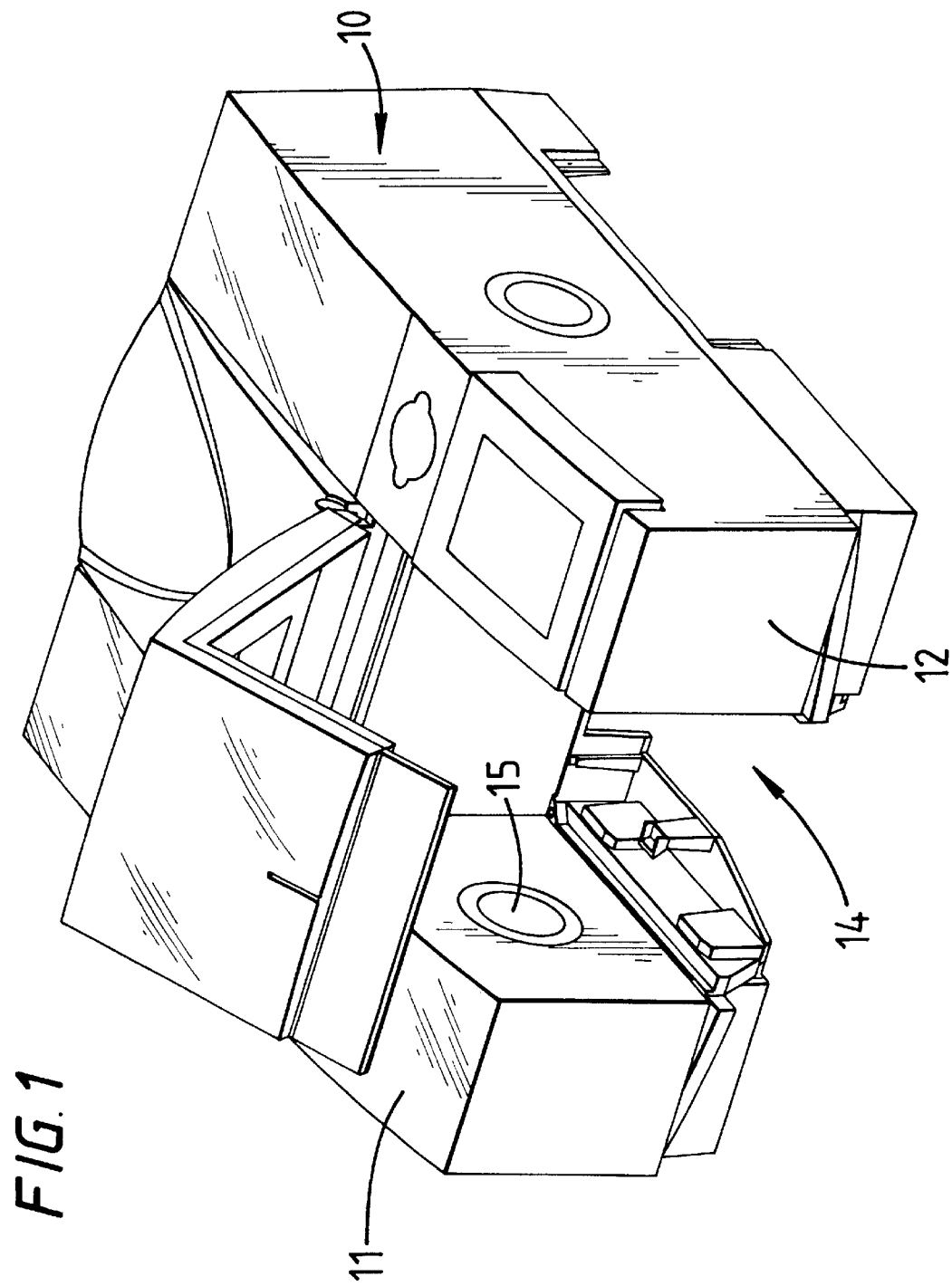
FIG. 1 is a schematic illustration of a spectrometer which an accessory in accordance with the present invention may be employed.

Referring to FIG. 1 of the drawings a spectrometer with which the present accessory can be employed has a housing 10 which accommodates the operative elements of the spectrometer. These include a source of infra-red radiation, a detector capable of detecting infra-red radiation and data processing means for processing signals received from the detector to provide output spectral data relating to the sample under analysis. The spectrometer can also have an associated PC (not shown) which provides a user interface and which can receive the output data and carry out processing of that data to provide spectral information. The housing 10 includes two forwardly projecting limbs 11 and 12 which define there between a sample station 14.

The innerside wall of each limb (11, 12) includes a window 15 through which analyzing radiation can pass. The present accessory to be described below is locatable in the sample station 14 so that analyzing radiation emitted through the window 15 in limb 11, passes to the accessory, is directed along a path to an HATR crystal in the accessory and then exit the accessory, to be received through another window 15 on the opposite limb 12 of the spectrometer where it is received by a detector.

The spectrometer shown in FIG. 1 includes an electrical connector which can connect to an accessory located in the sample station to enable electrical signals to be transferred between the accessory and the processor of the spectrometer. The way in which this operation functions is not at the heart of the present invention but is described in more detail in European Patent Application No. 98300745.1.

Referring to FIG. 2 an accessory for carrying out a HATR measurements has a housing 20 which accommodates a number of optical elements to be described below. Each upright side wall of the housing has an aperture 21,22, the aperture 21 when the accessory is placed in the sample station 14 allowing radiation from the radiation source of the spectrometer to pass into the accessory and the aperture 27 allowing radiation to exit from the accessory towards the detector of the spectrometer.

FIG. 3 illustrates the principal optical elements located within the housing 20 of the accessory. The optical elements include input optical elements comprising an input concave toroid mirror 25 which is pivotably mounted relative to the rear wall of the accessory housing, a fixed planar mirror 26, and a toroid/ellipsoidal fixed mirror 28. The optical elements also include output optical elements comprising a fixed toroid/ellipsoidal mirror 30, a fixed planar mirror 31 and a planar mirror 32 which is pivotably mounted relative to the rear wall of the housing 20.

Figure 6A:
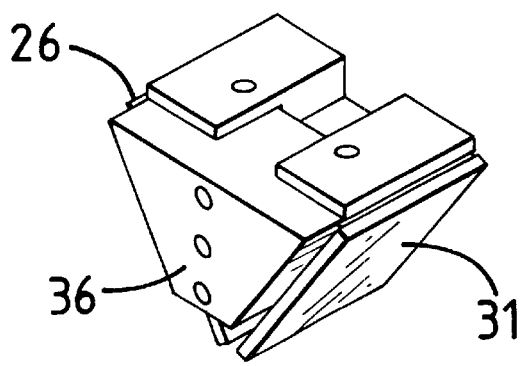
FIGS. 6a and 6b show the mounting of the fixed planar mirrors.
Figure 6B:
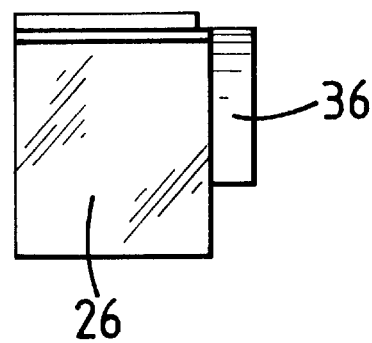
Figure 8:
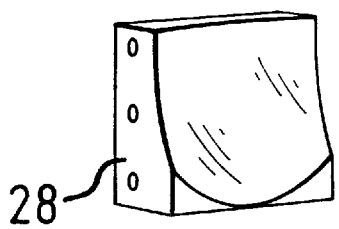
FIG. 8 is a perspective view showing one of the toroidal/ellipsoidal mirrors.

The fixed toroid/ellipsoidal mirrors 28 and 30 are each positioned to the rear wall of the accessory housing by dowels 34 and secured by a screw 33. One such mirror is shown also in perspective in FIG. 8. The two fixed planar mirrors 26 and 31 are secured by a bonding agent to the opposite inclined faces of a block 36 (see also FIG. 6). The block 36 is positioned to the rear face of the accessory housing by dowels and secured by a screw.

Figure 4A:
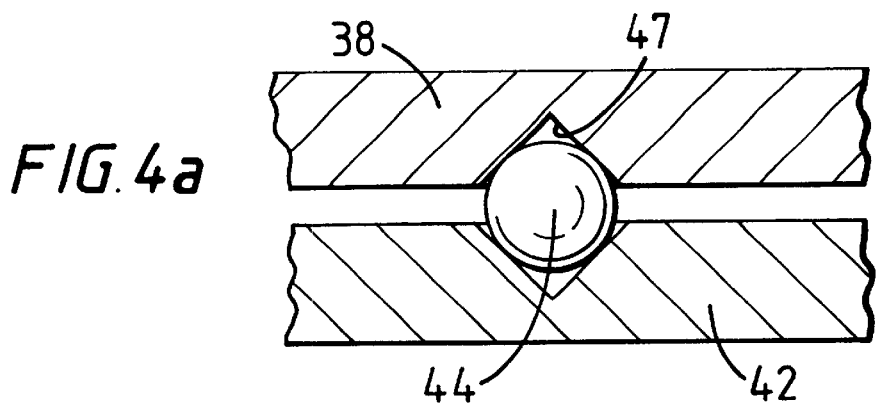
FIG. 4a is a sectional view on arrows 4a of FIG. 3.
Figure 4B:
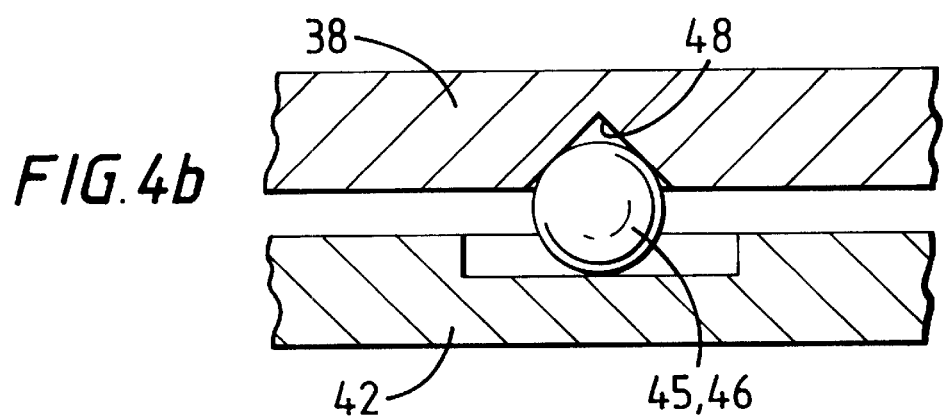
FIG. 4b is a sectional view on arrows 4b of FIG. 3.
Figure 4C:
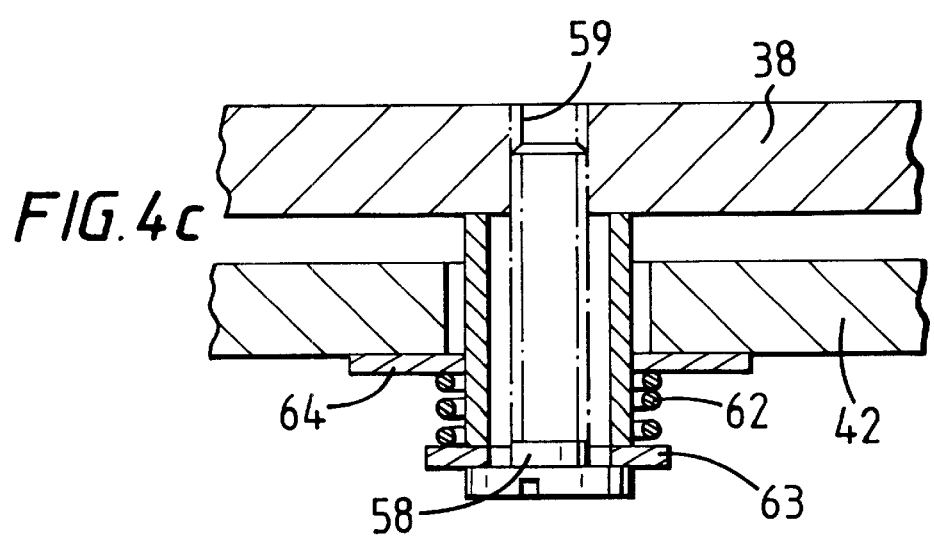
FIG. 4c is a sectional view on arrows 4c of FIG. 3.
Figure 5A:
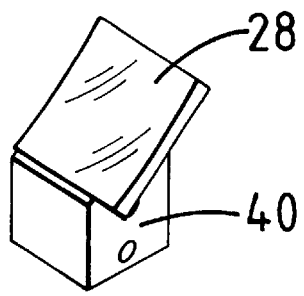
FIG. 5 shows the mounting of a toroidal mirror.
Figure 5B:
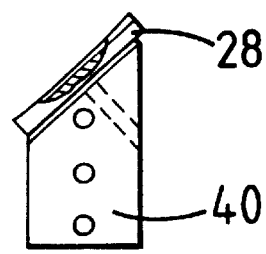
Figure 7A:
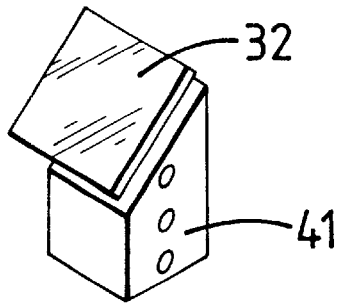
FIG. 7 shows the mounting of a planar mirror.
Figure 7B:
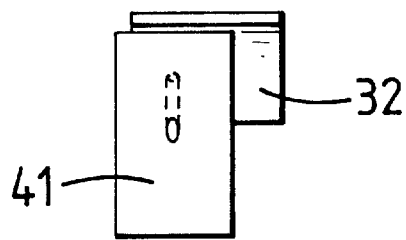
Figure 9A:
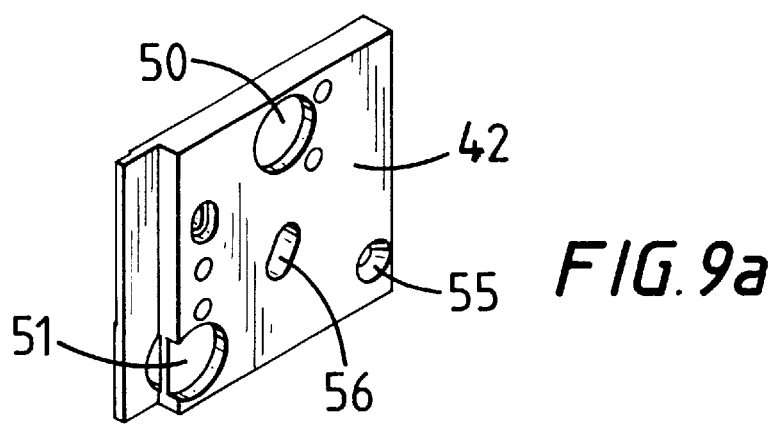
FIGS. 9a, 9b and 9c are respectfully rear perspective, front perspective and sectional views of one of the pivotable plates.
Figure 9B:
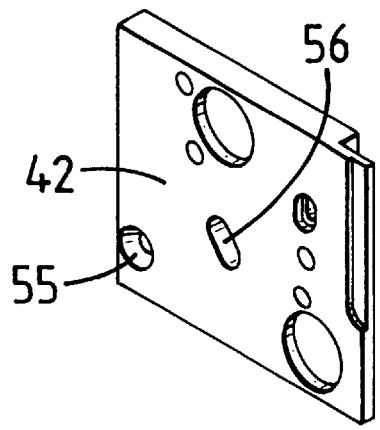
Figure 9C:
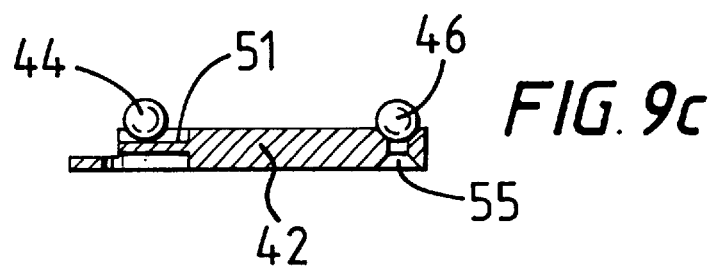

The toroid mirror 25 and the planar mirror 32 are each secured by a bonding agent to an inclined surface of a respective block 40,41 (see also FIGS. 5 and 7). Each block (40,41) is in turn secured to a generally square plate 42,43. The two plates (42,43) are each pivotably mounted relative to the rear wall of the accessory housing in a manner which will now be described with reference particularly to plate 42. A similar description applies in relation to plate 43. The plate 42 is mounted in spaced parallel relationship to the rear wall 38 of the accessory housing by means of three balls 44,45 and 46 located at the apices of a triangle. As shown in FIGS. 4a and 4b part of each ball locates in a conical recess (47,48) formed in the inner surface of the housing wall 38. The two balls 45 and 46 locate in a respective circular recess 50 and 51 formed in rear surface of the plate 42 (see also FIG. 9). The ball 44 locates in an inner conical portion of a through recess 55 formed in the bottom left hand corner of the plate 42. The ball 44 constitutes a pivot point about which the plate 42 can pivot. Generally centrally of the plate there is formed an elongate aperture 56 through which extends a screw 58 which engages a threaded aperture 59 formed in the rear wall of the accessory housing (FIG. 4c). The screw extends through the bore of a sleeve 60 which is biased by compression spring 62 extending between a washer 63 and a PTFE washer 64 extending around the aperture (56). This securing arrangement for the plate 42 allows the plate to pivot about the point 44 and the mounting arrangement of the plate against the balls 44 to 46 ensures that the plate when pivoted moves smoothly in a plane parallel to the rear surface of the accessory housing.

The plate 43 is mounted in a generally similar fashion although the arrangement is generally a mirror image of that of plate 42 so that the plate 43 can pivot in the opposite sense. Each plate 42,43 has an upwardly extending member between which extends an extension spring 66 which acts to maintain the lower inner corner portioning of the two plates in contact with a cam member 70. The cam member 70 is mounted on a shaft connected to a stepper motor (not shown). The cam member 70 comprises essentially three angularly spaced portions of different radii which are shown on radii R1, R2, and R3. Rotation of the cam member by means of the stepper motor successively brings different portions of the circumference of the cam into contact with the inner edge portions of the two plates 42,43 thereby pivoting those plates to a different orientation. As a consequence the orientation of each mirror is 25,32 adjusted as the plate is rotated.

An HATR crystal 75 is mounted above the block 36 arranging the mirrors 26,31. The crystal is mounted either on a plate when solid samples are to be analysed or in a trough when liquid samples are to be analysed. The samples to be analysed are located on the top surface of the crystal. The crystal mounting incorporates a data storage medium in which is stored data indicative of the crystal.

In operation the accessory is mounted in the sample station 14 of the spectrometer shown in FIG. 1. An electrical connector on the accessory housing makes contact with a corresponding connector on the spectrometer housing to allow electrical communication between the data storage medium in the accessory and the processor of the spectrometer. This allows the processor of the spectrometer to read data relating to the accessory eg type of crystal, mounted on the top plate above the fixed mirrors 26, 31, and to provide appropriate signals to the stepper motor to cause rotation of the cam 70 to a position in which the plates 42 and 43 are so oriented that the radiation 78 reflected by the mirrors 25, 26, 28 enters the HATR crystals at the correct angle of incidence. If no crystal is present on the crystal mounting the motor drives the cam to a datum position. Once, the mirrors have been so set a spectral measurement is carried out by passing analyzing radiation into the accessory and through the HATR crystal 75 in a manner which will be apparent to those skilled in the art. When a change of crystal occurs signals from the storage medium of the crystal mounting plate are fed to the processor and the processor sends instructing signals to the stepper motor to cause rotation of the cam 70 to the appropriate position for that crystal. In the arrangement shown in FIG. 3 the mirrors 25, 26, 31 and 32 act as beam steerers. The mirrors 28 and 30 act as focusing and de-focusing optical elements respectively. The mirror 28 operates to produce an approximately elliptical focus on the internal end face 76 of the crystal 75. The angle shown as θ changes when cam 70 is rotated to change the inclination of the mirrors 25, 32.

It will be appreciated that the reflecting surfaces will have an appropriate coating for the radiation employed. This can be aluminum for infra-red radiation.

It will thus be seen that the present arrangement provides an automatic technique for adjusting the mirrors to a position which provides a correct angle of incidence for radiation into the HATR crystal. The particular technique used ensures that the pivoting of the mirrors is carried out in a repeatable and synchronized manner. In the particular example described the stepper motor rotates the variable radius wheels to one of the three positions which correspond to three different angles of incidence on HATR crystal. Each of the different radii extend to an angle of approximately 20° so that the step accuracy of the motor is not an important factor. Furthermore, each radius is held constant over several hundred steps so that the repeatability of the measurements is very good.

Figure 10:
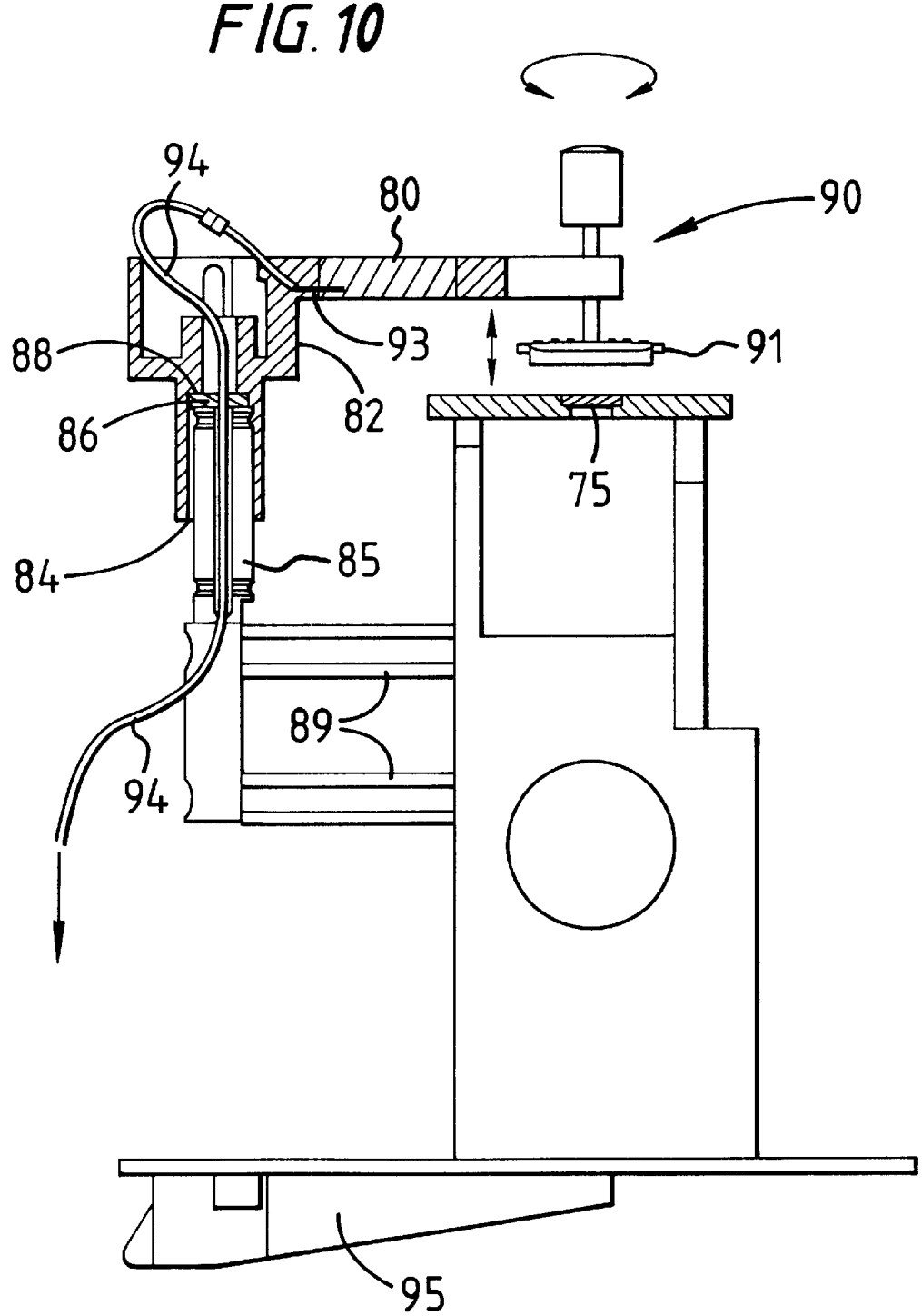
FIG. 10 is a side elevation of an arrangement for applying a force to a solid sample.

When solid samples are being investigated it is usual to apply a force to the sample to maintain its contact with the crystal. FIG. 10 shows an arrangement for producing an accurately repeatable force.

This comprises an arm 80 integrally formed with a cylindrical mounting element 82. The mounting has a through bore 84 the lower portion of which receives the upper end of shaft 85. The shaft has at its upper end a teflon washer 86 which sits against a shoulder 88. The shaft 85 is carried by two horizontal elements 89 which are secured to the accessory housing. The above arrangement allows the arm 80 to swing about the axis of the shaft 85 in a horizontal plane.

The arm carries at its free end a thumb screw adjustment mechanism 90 which can be used to adjust the vertical position of a load shoe 91. The load shoe can thus be lowered into contact with a sample on the crystal 75.

The arm has bonded thereto a strain gauge 93.

The strain gauge is connected electrically by a electrical wiring 94 and an electrical connecter 95 to the processor of the spectrometer.

In use when a solid sample is placed on the crystal 75 the arm 80 is positioned so that the load shoe 91 is over the sample. The thumb screw mechanism 90 is operated to lower the shoe into contact with the sample. The strain gauge responds to bending of the arm and electrical signals from the strain gauge 93 are fed back to the instrument processor which calculate the force being applied to the sample. This force is displayed on the display unit of an associated PC. Thus an operator can accurately set the force applied to the sample ready for a measurement and this can be done in an accurately repeatable manner.

What is claimed is:

1. An accessory for use with a spectrometer which has a sample station in which the accessory can be located, said accessory comprising a mounting for receiving an ATR crystal, first optical elements for directing an incoming beam of analyzing radiation to said crystal, second optical elements for directing a beam of radiation exiting the crystal to an outlet, at least one of the first optical elements and at least one of the second optical elements being pivotable, and means operable to cause pivoting movement of said pivotable elements so that the beam of analyzing radiation is caused to be incident on said crystal at an angle appropriate for particular crystal employed or the measurement to be made;

said first optical elements include a first mirror fixed to a first plate which is pivotally mounted on a housing of the accessory, and the second optical element includes a second pivotable mirror mounted on a second plate which is pivotally mounted on the housing of the accessory; and said pivoting means comprise a rotatable cam member disposed at least partially between and in contact with said plates.

2. An accessory according to claim 1 wherein the cam member may include a plurality of angularly spaced portions of different radii whereby rotation of the cam member causes said plates to assume an orientation which is different according to which portion of the cam member contacting said plates.

3. An accessory according to claim 1 wherein the cam member is rotatable by a motor.

4. An accessory according to claim 1 wherein the first mirror is a toroidal mirror and the second mirror is a planar mirror.

5. An accessory for use with a spectrometer which has a sample station in which the accessory can be located, said accessory comprising a mounting for receiving an ATR crystal, first optical elements for directing an incoming beam of analyzing radiation to said crystal, second optical elements for directing a beam of radiation exiting the crystal to an outlet, at least one of the first optical elements and at least one of the second optical elements being pivotable, and means operable to cause pivoting movement of said pivotable elements so that the beam of analyzing radiation is caused to be incident on said crystal at an angle appropriate for particular crystal employed or the measurement to be made; and electrical connectors which when the accessory is located in the sample station make contact with a connector on the spectrometer and the crystal has incorporated therein a data storage medium in which is stored data indicative of the crystal, the arrangement being such that when the accessory is located in the sample station the processor of the spectrometer can read said stored data and can transmit activating signals to cause the pivotable mirrors to be adjusted to a position appropriate to the crystal.

* * * * *